US008544474B2

(12) United States Patent
Sandhu et al.

(10) Patent No.: US 8,544,474 B2
(45) Date of Patent: Oct. 1, 2013

(54) SYSTEMS AND METHODS FOR MAGNETIC-ASSISTED THERAPEUTIC AGENT DELIVERY

(75) Inventors: Gurpreet S. Sandhu, Rochester, MN (US); David R. Holmes, Jr., Rochester, MN (US); Robert D. Simari, Rochester, MN (US); Nicole P. Sandhu, Rochester, MN (US); David R. Holmes, III, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 445 days.

(21) Appl. No.: 12/809,197

(22) PCT Filed: Dec. 19, 2008

(86) PCT No.: PCT/US2008/087628
§ 371 (c)(1),
(2), (4) Date: Sep. 21, 2010

(87) PCT Pub. No.: WO2009/086071
PCT Pub. Date: Jul. 9, 2009

(65) Prior Publication Data
US 2011/0144411 A1    Jun. 16, 2011

Related U.S. Application Data

(60) Provisional application No. 61/008,423, filed on Dec. 20, 2007.

(51) Int. Cl.
*A61B 19/00*    (2006.01)

(52) U.S. Cl.
USPC ............................ 128/899; 128/897; 600/13

(58) Field of Classification Search
USPC ........ 600/9–15, 407; 128/897–899; 436/526
See application file for complete search history.

(56) References Cited

U.S. PATENT DOCUMENTS

| 5,921,244 A | 7/1999 | Chen et al. |
| 6,190,315 B1 | 2/2001 | Kost et al. |
| 6,203,487 B1 | 3/2001 | Consigny |
| 6,216,030 B1 | 4/2001 | Howard et al. |

(Continued)

FOREIGN PATENT DOCUMENTS

| DE | 11 2005 002270 T5 | 8/2007 |
| EP | 1674 128 A1 | 6/2006 |

OTHER PUBLICATIONS

Pislaru et al., "Magnetic forces enable rapid endothelialization of synthetic vascular grafts," *Circulation*, Jul. 4, 2006; 114(1 Suppl.): I314-8.

(Continued)

*Primary Examiner* — Charles A Marmor, II
*Assistant Examiner* — Shannon Canty
(74) *Attorney, Agent, or Firm* — Mueting, Raasch & Gebhardt, P.A.

(57) ABSTRACT

Systems and methods that provide magnetically-enhanced delivery of therapeutic agents to selected tissue are disclosed. The systems and methods involve the use of carrier devices and release devices and two different magnetic fields to move magnetic particles into selected tissue. Movement of the magnetic particles (and any associated therapeutic agent) into the tissue may be assisted by both magnetic attractive forces as well as magnetic repulsive forces.

20 Claims, 2 Drawing Sheets

(56) References Cited

U.S. PATENT DOCUMENTS

| | | |
|---|---|---|
| 7,189,198 B2 | 3/2007 | Harburn et al. |
| 7,218,962 B2 | 5/2007 | Freyman |
| 2004/0050394 A1 | 3/2004 | Jin |
| 2005/0113630 A1 | 5/2005 | Fox et al. |
| 2005/0271732 A1 | 12/2005 | Seeney et al. |
| 2006/0041182 A1 | 2/2006 | Forbes et al. |
| 2006/0142748 A1* | 6/2006 | Foreman et al. ............ 606/27 |
| 2006/0204442 A1 | 9/2006 | Tapolsky et al. |
| 2006/0228421 A1 | 10/2006 | Seeney et al. |
| 2006/0264690 A1 | 11/2006 | Ochi |
| 2006/0286137 A1 | 12/2006 | Sandhu et al. |
| 2007/0196281 A1 | 8/2007 | Jin et al. |

OTHER PUBLICATIONS

Pislaru et al., "Magnetically Targeted Endothelial Cell Localization in Stented Vessels," *J. Am. Coll. Cardiol*, Nov. 7, 2006; 48(9): 1839-45. Available online Oct. 16, 2006.

International Search Report issued by the Korean Patent Office as the International Search Authority on Aug. 7, 2009 Patent Application No. PCT/US2008/087628, filed Dec. 19, 2008; 4 pgs.

International Preliminary Report on Patentability issued by the International Bureau of WIPO on Jun. 22, 2010, Patent Application No. PCT/US2008/087628, filed Dec. 19, 2008; 6 pgs.

\* cited by examiner

SYSTEMS AND METHODS FOR MAGNETIC-ASSISTED THERAPEUTIC AGENT DELIVERY

RELATED APPLICATION

The present application is a U.S. National Stage Application of International Application No. PCT/US2008/087628, titled SYSTEMS AND METHODS FOR MAGNETIC-ASSISTED THERAPEUTIC AGENT DELIVERY, filed on Dec. 19, 2008, published in the English language on Jul. 9, 2009 as International Publication No. WO 2009/086071 A2, which claims the benefit under 35 U.S.C. §119(e) of U.S. Provisional Patent Application No. 61/008,423 filed on Dec. 20, 2007 and titled SYSTEMS AND METHODS FOR MAGNETIC-ASSISTED THERAPEUTIC AGENT DELIVERY, both of which are hereby incorporated by reference in their entirety.

The present invention relates generally to the field of therapeutic agent delivery and, more particularly, to magnetic-assisted delivery of one or more therapeutic agents to selected tissue.

Magnetically-assisted delivery of drugs, cells, etc. has been described in various documents such as U.S. Pat. No. 5,921,244 (Chen et al.); U.S. Pat. No. 6,203,487 (Consigny); and U.S. Pat. No. 7,218,962 (Freyman). Other aspects of magnetically-assisted delivery have been described in. e.g., U.S. Patent Application Publication Nos. US 2006/0041182 (Forbes et al.) and US 2006/0264690 (Ochi).

Such methods typically involve the use of magnetic force from only one direction and are limited in their ability to move magnetic particles through tissue.

SUMMARY OF THE INVENTION

The present invention provides systems and methods that provide magnetically-enhanced delivery of therapeutic agents to selected tissue. The systems and methods involve the use of carrier devices and release devices and two different magnetic fields to move magnetic particles into selected tissue. Movement of the magnetic particles (and any associated therapeutic agent) into the tissue is preferably assisted by both magnetic attractive forces as well as magnetic repulsive forces as discussed herein.

A variety of different magnetic particles may be used in conjunction with the present invention, with the magnetic particles being associated with one or more therapeutic agents. When describing that the magnetic particles are "associated with" a therapeutic agent (or vice versa), it is meant that the magnetic particles may themselves be a therapeutic agent (e.g., a magnetic molecule, etc.), the therapeutic agent may be carried on or in a magnetic particle, and/or the therapeutic agent may carry one or more magnetic particles.

The "therapeutic agents" used in connection with present invention may be any substance intended to have a therapeutic effect on the patient, e.g., pharmaceutical compositions, genetic materials, biologics, and other substances. "Pharmaceutical compositions," as used herein, may include chemical formulations intended to have a therapeutic effect such as intrathecal antispasmodics, pain medications, chemotherapeutic agents, and the like. Pharmaceutical compositions are often configured to function effectively in an implanted environment by possessing various characteristics including: stability at body temperature to retain therapeutic qualities; concentration to reduce the frequency of replenishment; and the like. "Genetic materials," as used herein, may include substances intended to have a direct or indirect genetic therapeutic effect such as genetic vectors, genetic regulator elements, genetic structural elements, DNA, and the like. "Biologics," as used herein, may include substances that are living matter, or derived from living matter, and offer a therapeutic effect to the patient such as stem cells, platelets, hormones, biologically produced chemicals, and the like. "Other substances" may include most any other substance that is intended to have a therapeutic effect, yet does not clearly fit within one of the categories identified above. Examples of other substances may include saline solutions, fluoroscopy agents, and the like.

In one aspect, the present invention provides a system for magnetically-assisted delivery of a therapeutic agent. The system includes a carrier device having a carrier surface and first magnetic field generator generating a first magnetic field with magnetic flux lines extending through the carrier surface, wherein the first magnetic field has a first magnetic field strength at the carrier surface; a plurality of discrete magnetic particles attracted to the carrier surface by the first magnetic field, wherein the magnetic particles are associated with a therapeutic agent; a release device with a second magnetic field generator generating a second magnetic field with magnetic flux lines extending through a release surface of the release device, wherein the second magnetic field generator is capable of generating the second magnetic field with a second magnetic field strength at the carrier surface that is greater than the first magnetic field strength at the carrier surface when the release surface is located a distance of 2 centimeters or less from the carrier surface.

In various embodiments, the systems described above may include one or more of the following features/components: the second magnetic field generator may be capable of generating the second magnetic field with a second magnetic field strength at the carrier surface that is greater than the first magnetic field strength at the carrier surface when the release surface is located a distance of 5 centimeters or less from the carrier surface; the second magnetic field generator may be capable of generating the second magnetic field with a second magnetic field strength at the carrier surface that is greater than the first magnetic field strength at the carrier surface when the release surface is located a distance of 10 centimeters or less from the carrier surface; the second magnetic field generator may be capable of generating the second magnetic field with a second magnetic field strength at the carrier surface that is greater than the first magnetic field strength at the carrier surface when the release surface is located a distance of 15 centimeters or less from the carrier surface; the first magnetic field generator may include magnetic material that generates a static magnetic field; the first magnetic field generator may include an electromagnet; the second magnetic field generator may include magnetic material that generates a static magnetic field; the second magnetic field generator may include an electromagnet; the first magnetic field generator may include permanently magnetized material and the second magnetic field generator may include an electromagnet; a controller operably connected to one or more electromagnets to control the first and/or second magnetic field strength and/or polarity (optionally using a predetermined protocol), etc.

In another aspect, the present invention provides a method of delivering a therapeutic agent. The method may include positioning a carrier surface of a carrier device proximate selected internal tissue, wherein magnetic flux lines of a selected magnetic pole of a first magnetic field extend through the carrier surface; magnetically retaining a therapeutic agent to the carrier surface, wherein the therapeutic agent is associated with a plurality of magnetic particles; positioning a release device that comprises a release surface proximate the selected internal tissue, wherein the selected internal tissue is located between the release surface and the carrier surface, and wherein the release device comprises a second magnetic field generator generating a second magnetic field that extends through the release surface and towards the carrier surface; and delivering at least a portion of the therapeutic substance to the selected internal tissue by magnetically attracting at least a portion of the plurality of magnetic particles towards the release surface; wherein, proximate the carrier surface, the second magnetic field has a magnetic field strength greater than a magnetic field strength of the first magnetic field; and wherein the second magnetic field extending through the release surface comprises a magnetic pole facing the carrier device that is the same as the selected magnetic pole of the carrier device.

In various embodiments, the methods described above may include one or more of the following features: changing the second magnetic field strength over time after positioning the carrier surface proximate selected internal tissue; reversing the magnetic pole of the second magnetic field after positioning the carrier surface proximate selected internal tissue; reversing the magnetic pole of the second magnetic field three or more times while the selected tissue is located between the carrier surface and release surface; holding the first magnetic field strength substantially constant at the carrier surface; reducing the magnetic field strength of the first magnetic field extending through the carrier surface after positioning the carrier surface proximate the selected internal tissue; terminating the first magnetic field after positioning the carrier surface proximate selected internal tissue; generating the first magnetic field by magnetic material that generates a static magnetic field; generating the second magnetic field by magnetic material that generates a static magnetic field; etc.

The words "preferred" and "preferably" as used herein refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, "a," "an," "the," "at least one," and "one or more" are used interchangeably. Thus, for example, "a carrier surface" may include one or more carrier surfaces, "a therapeutic agent" may include one or more therapeutic agents, etc.

The term "and/or" as used herein means one or all of the listed elements or a combination of any two or more of the listed elements.

The above summary is not intended to describe each embodiment or every implementation of the present invention. Rather, a more complete understanding of the invention will become apparent and appreciated by reference to the following Description of Exemplary Embodiments and claims in view of the accompanying figures of the drawing.

BRIEF DESCRIPTION OF THE VIEWS OF THE DRAWING

The present invention will be further described with reference to the views of the drawing, wherein.

DESCRIPTION OF EXEMPLARY EMBODIMENTS

Figure 1:
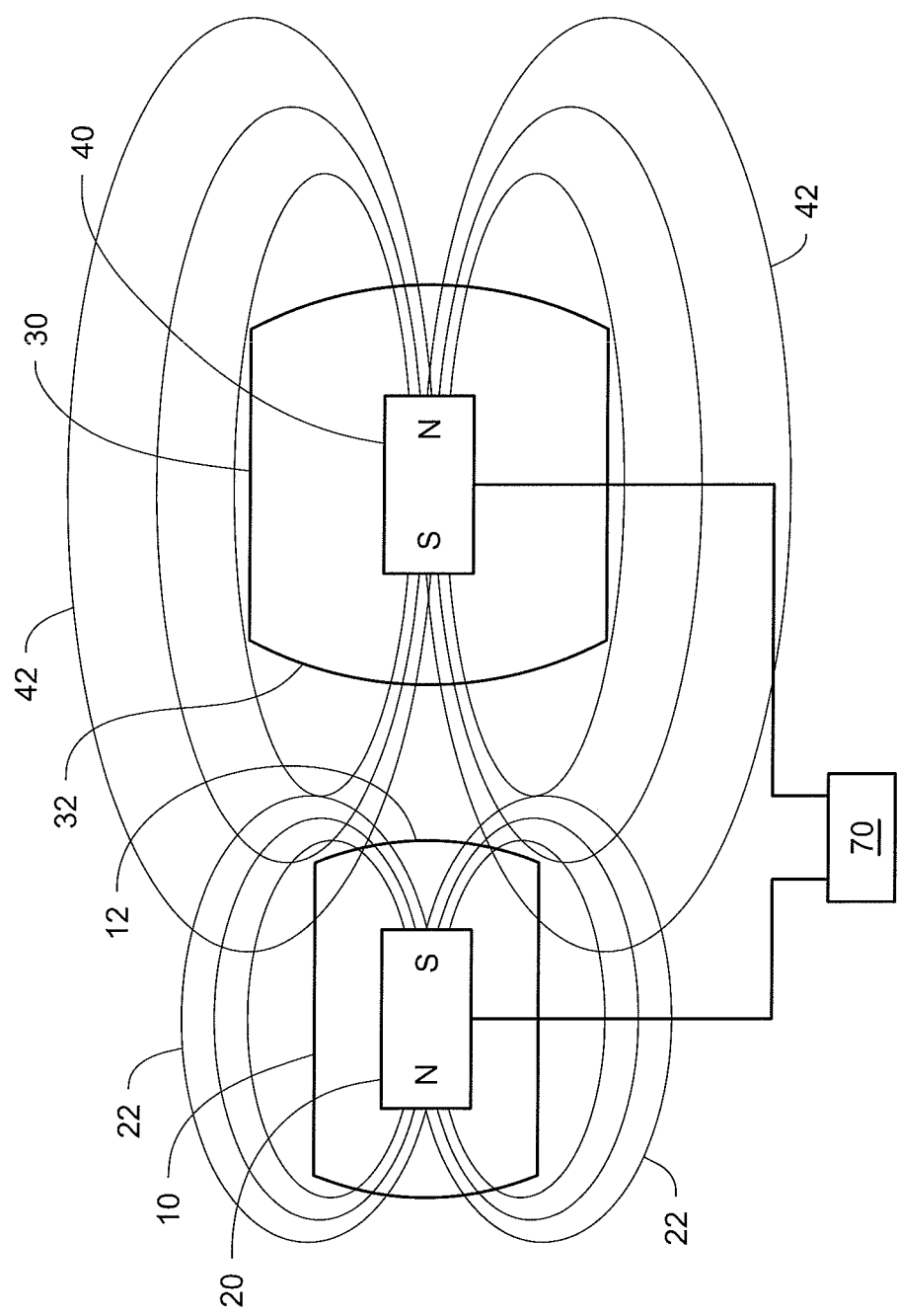
FIG. 1 is a schematic diagram of one exemplary system for magnetically-assisted delivery of a therapeutic agent.

In the following detailed description of exemplary embodiments of the invention, reference is made to the accompanying figures of the drawing which form a part hereof, and in which are shown, by way of illustration, specific embodiments in which the invention may be practiced. It is to be understood that other embodiments may be utilized and structural changes may be made without departing from the scope of the present invention.

One exemplary embodiment of a system for magnetically-assisted delivery of a therapeutic agent is schematically depicted in FIG. 1. The system includes a carrier device 10 having a carrier surface 12. The carrier device 10 also includes a magnetic field generator 20. The magnetic field generator 20 generates a magnetic field represented by magnetic flux lines 22 that extend from two magnetic poles N & S. It may be preferred that the magnetic field generator 20 be arranged within the carrier device 10 such that the magnetic flux lines 22 from only one of the magnetic poles of the magnetic field generator 20 extend through the carrier surface 12 of the carrier device 10.

The system depicted in FIG. 1 also includes a release device 30 that includes a second magnetic field generator 40. The second magnetic field generator 40 generates a second magnetic field represented by magnetic flux lines 42 that extend from two magnetic poles N & S. It may be preferred that the magnetic field generator 40 be arranged within the release device 30 such that the magnetic flux lines 42 from only one of the magnetic poles of the magnetic field generator 40 extend through the release surface 32 of the release device 30.

The system depicted in FIG. 1 also includes an optional controller 70 that may be used to control one or both of the magnetic field generators 20 and 40 such that the magnetic fields as discussed herein are provided.

The present invention can be used to enhance delivery of one or more therapeutic agents to selected tissue by using the magnetic fields of the carrier device and the release device. As discussed herein, it may be preferred that the relative strength of the two magnetic fields generated by the first magnetic field generator 20 and the second magnetic field generator 40 be such that the second magnetic field strength at the carrier surface 12 is greater than the strength of the first magnetic field at the carrier surface 12.

Figure 2:
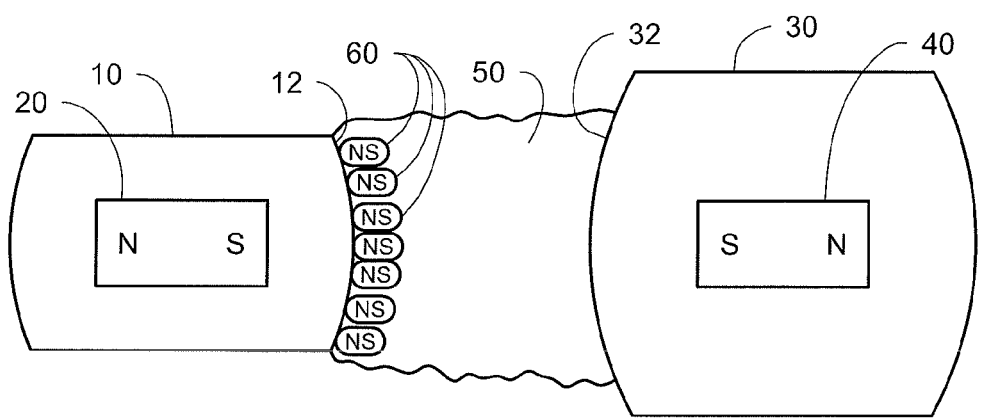
FIG. 2 is a schematic diagram of the system of FIG. 1 deployed with selected tissue located between the carrier device and the release device.

Turning to FIG. 2, the carrier device 10 and the release device 30 are deployed with selected tissue located between the carrier surface 12 of the carrier device 10 and the release surface 32 of the release device 30. Magnetic particles 60 are preferably magnetically attracted to the carrier surface 12 (although other attachment mechanisms/techniques may be used in place of or in addition to magnetic attraction). As discussed herein, the magnetic particles 60 may be associated with one or more therapeutic agents that are to be delivered into the selected tissue with the assistance of magnetic forces.

The carrier device 10 and/or the release device 30 may be designed for use in vivo or ex vivo depending on the selected tissue 50. In some embodiments, both the carrier device 10 and the release device 30 may be designed for internal (in vivo) deployment to assist with the delivery of one or more therapeutic agents to internal selected tissue. In other embodiments, one of the devices, e.g., the release device 30, may be designed for external (ex vivo) deployment in conjunction with a carrier device 10 that is designed for internal deployment (or vice versa). In still other embodiments, both the carrier device 10 and the release device 30 may be designed for external deployment.

The magnetic particles 60 (and any therapeutic agent associated with the particles 60) may be attached to the carrier surface 12 before the carrier surface 12 is positioned proximate the selected tissue 50 into which the magnetic particles are to be used to deliver the therapeutic agent(s). Alternatively, the magnetic field provided by the magnetic field generator 20 may be used to attract the magnetic particles 60 to the carrier surface 12 after the carrier device 10 is positioned proximate the selected tissue 50. For example, the magnetic particles 60 may be delivered to the carrier surface 12 through the bloodstream or other pathways/mechanisms after the carrier device 10 is located proximate the selected tissue 50.

Figure 3:
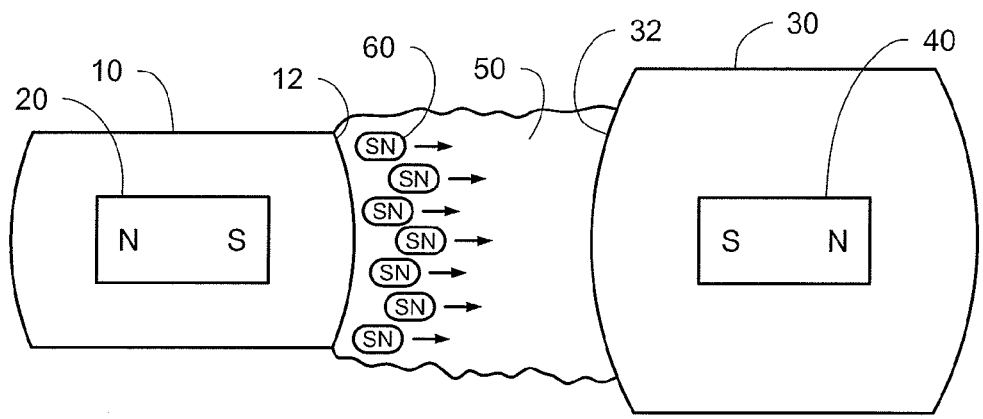
FIG. 3 is a schematic diagram of the system of FIG. 2 depicting magnetic particles being delivered to the selected tissue.

With the carrier device 10 and the release device 30 positioned such that the selected tissue 50 is located between the carrier surface 12 and the release surface 32, the magnetic fields provided by the respective magnetic field generators in the carrier device 10 and the release device 30 may be such that the magnetic particles 60 release from the carrier surface 12 and are magnetically attracted towards the release surface 32 of the release device 30 as depicted in FIG. 3. After releasing from the carrier surface 12, it may be preferred that the orientation of the magnetic particles 60 flips such that the north pole of each magnetic particle 60 faces the release surface 32 (in comparison to FIG. 2 in which the north pole of each magnetic particle 60 faces the carrier surface 12).

It may be preferred that the magnetic poles defined by the two different magnetic fields be the same, i.e., that the magnetic pole of the magnetic field generator 20 that faces or is proximate the carrier surface 12 of the carrier device 10 is the same as the magnetic pole of the magnetic field generator 40 that faces or is proximate the release surface 32 of the release device 30. In the embodiment depicted in FIGS. 1-3, the south poles of the different magnetic fields face each other, although it should be understood that the north poles could alternatively face each other across or through the selected tissue.

The magnetic particles are preferably released from the carrier surface 12 and drawn towards the release device 30 and, thus, into the selected tissue 50 located between the carrier surface 12 and the release surface 32. In making that transition, it is theorized that the dipoles of the magnetic particles 60 essentially flip because the second magnetic field emanating from the release device 30 is of the same polarity as the first magnetic field used to attract the magnetic particles 60 to the carrier surface 12.

The result of the change in orientation of the poles on the magnetic particles 60 is that the magnetic particles 60 are preferably drawn into the selected tissue 50 by magnetic attraction to the release device 30 and, at the same time, the magnetic particles are preferably driven into the selected tissue 50 by magnetic repulsion between the magnetic particles 60 and the carrier surface 12. That combination of magnetic attraction and magnetic repulsion may advantageously combine to draw/drive the magnetic particles 60 (and any therapeutic agents associated therewith) further into the selected tissue 50 than either of these forces could if used alone.

The relative strengths of the magnetic fields generated by the carrier device 10 and the release device 30 may preferably be characterized in terms of magnetic field strength as measured at the carrier surface 12. It may be preferred, for example, that the magnetic field strength of the second magnetic field (emanating from the release device 30) is greater at the carrier surface 12 than the magnetic field strength of the first magnetic field emanating from the carrier device 10. It may further be preferred that the relative strengths between the first and second magnetic fields be determined when the carrier device 10 and the release device 30 are positioned such that the release surface 32 is located a distance of 2 centimeters or less (or, in some embodiments: 5 centimeters or less, 10 centimeters or less, 15 centimeters or less, 0.5 meter or less, 1 meter or less, or even 2 meters or less) from the carrier surface 12.

The devices of the present invention may be made of any suitable material (including, e.g., polymeric materials, metals, metal alloys, ceramics, composites, etc.). Although both the carrier device and the release device are depicted as including distinct magnetic field generators (20 and 40, respectively), it should be understood that the magnetic field generators may or may not be provided as separate and distinct components located within or in connection with the carrier device and/or release device.

In some embodiments, the magnetic field generators of the carrier device and/or release device may be provided in the form of one or more materials that are magnetic, i.e., that either exhibit a permanent magnetic field or that are capable of exhibiting a temporary magnetic field. The entire device, or selected portions thereof, may be manufactured from the one or more magnetic materials to provide a magnetic field generator. For example, a predetermined quantity of magnetite or an alloy thereof may be included in the construction of the device. Other materials may be utilized in addition to or in place of magnetite to provide the desired magnetic properties. Such materials may be temporary magnetic materials or permanent magnetic materials. Some examples of suitable magnetic materials include, e.g., magnetic ferrite or "ferrite" which is a substance consisting of mixed oxides of iron and one or more other metals, e.g., nanocrystalline cobalt ferrite. However, other ferrite materials may be used.

Other magnetic materials which may be utilized in the construction of the magnetic field generators in the devices may include, but are not limited to, ceramic and flexible magnetic materials made from strontium ferrous oxide which may be combined with a polymeric substance (such as, e.g., plastic, rubber, etc.); NdFeB (this magnetic material may also include Dysprosium); neodymium boride; SmCo (samarium cobalt); and combinations of aluminum, nickel, cobalt, copper, iron, titanium, etc.; as well as other materials.

If the device is made of metals such as, e.g., stainless steel, nickel titanium alloys (e.g., NITINOL), etc. or other magnetizable materials, the magnetizable materials may be rendered sufficiently magnetic by subjecting the magnetizable material to a sufficient electric and/or magnetic field. Such a field may imbue the magnetizable materials (or a portion thereof) with magnetic properties without the need to include the permanent magnetic materials described above.

If the devices are designed to be deployed to internal (in vivo) locations within a human or animal body, their outer surfaces may preferably be biocompatible. Unfortunately, many magnetic materials may not be biocompatible. The non-biocompatible magnetic materials within any such device may be contained within or covered by a biocompatible material that does not significantly limit or interfere with the magnetic fields emanating from the devices such that the devices exhibit the desired magnetic fields. Biocompatible coatings for use in connection with devices of the present invention may include, e.g., various biocompatible polymers, metals, and other synthetic, natural, or biologic materials.

In some embodiments, the magnetic field generators in one or both of the carrier device 10 and the release device 30 may be adjustable such that the magnetic field strength emanating from the carrier surface 12 and/or the release surface 32 is adjustable. Such adjustability may be achieved by providing a magnetic field generator in the form of, e.g. an electromagnet. Still other ways of providing adjustability may include, e.g., the use of shields, etc. with a static magnetic field generator.

Regardless of the actual form of the magnetic field generator, the magnetic field produced by the magnetic field generators may be described as static (i.e., in which the magnetic field strength does not vary significantly—this type of field may be associated with, e.g., permanent magnets). In still other embodiments, the magnetic field strength may be dynamic, i.e., the magnetic field strength may change over time in response to a controller or other mechanism. For example, the controller 70 (see FIG. 1) could be operably connected to one or both magnetic field generators 20 and 40 to provide magnetic fields with selected magnetic field strengths. Such a controller 70 could also or alternatively be used to control the polarity of the magnetic fields to provide like magnetic poles facing each other through the carrier surface 12 and the release surface 32 as discussed herein.

In some embodiments, the magnetic field strength of either or both the first and second magnetic fields may be changed over time. Those changes to magnetic field strength may include, e.g., increases and/or decreases in magnetic field strength. In still another variation, the polarity of the either or both the first and second magnetic fields may be reversed. Such changes in magnetic field strength and/or polarity reversals may be repeated one, two, three, or even more times if the field strength changes and/or polarity reversals enhance delivery of the magnetic particles and their associated therapeutic agents to the selected tissue.

If the therapeutic agents associated with the magnetic particles are cells, the cell may be any biologic cell that is itself capable of exhibiting a magnetic field, being modified to incorporate one or more magnetic particles that include a magnetic field, or that can be attached to a magnetic particle or cell that includes a magnetic particle that exhibits a magnetic field. The cells used in connection with the present invention may be, e.g., endothelial cells, ectoderm-, mesoderm-, endoderm-derived cells. Additionally, any stem or mature cell originating from various primitive cell layers in animals or humans may be modified to be useful in connection with the present invention. In other variations, the cells used in connection with the invention may be engineered to carry new genes that may secrete products capable of treating disease, e.g., heart failure, coronary artery disease, cancer, etc.

A variety of techniques for modification of cells such that the cells become associated with magnetic particles are known and are described in, e.g., U.S. Patent Application Publication No. US 2006/0286137 A1 (Sandhu et al.). As discussed therein, magnetic particles may be incorporated into the cell or attached to the cell surface by procedures known to those skilled in the art. In certain embodiments, magnetic particles may be fed to the target cells or temporary pores may be created in the cell membrane of the target cell by electroporation. In other embodiments, magnetic particles may be attached to the cell surface via antibody binding to cell membrane receptors or through chemical conjugation of the magnetic particle to the cell membrane.

The complete disclosure of the patents, patent documents, and publications cited in this document are incorporated by reference in their entirety as if each were individually incorporated.

Exemplary embodiments of this invention have been discussed and reference has been made to possible variations within the scope of this invention. These and other variations and modifications in the invention will be apparent to those skilled in the art without departing from the scope of the invention, and it should be understood that this invention is not limited to the illustrative embodiments set forth herein. Accordingly, the invention is to be limited only by the claims provided below and equivalents thereof.

The invention claimed is:

1. A system for magnetically-assisted delivery of a therapeutic agent, the system comprising:
a carrier device comprising a carrier surface and first magnetic field generator generating a first magnetic field comprising magnetic flux lines extending through the carrier surface, wherein the first magnetic field comprises a first magnetic field strength at the carrier surface;
a plurality of discrete magnetic particles attracted to the carrier surface by the first magnetic field, wherein the discrete magnetic particles are associated with a therapeutic agent;
a release device comprising a second magnetic field generator generating a second magnetic field comprising magnetic flux lines extending through a release surface of the release device, wherein the second magnetic field comprises a second magnetic field strength at the carrier surface that is greater than the first magnetic field strength at the carrier surface when the release surface is located a distance of 15 centimeters or less from the carrier surface.

2. A system according to claim 1, wherein the second magnetic field generator is capable of generating the second magnetic field such that the second magnetic field strength at the carrier surface that is greater than the first magnetic field strength at the carrier surface when the release surface is located a distance of 5 centimeters or less from the carrier surface.

3. A system according to claim 1, wherein the second magnetic field generator is capable of generating the second magnetic field such that the second magnetic field strength at the carrier surface that is greater than the first magnetic field strength at the carrier surface when the release surface is located a distance of 10 centimeters or less from the carrier surface.

4. A system according to claim 1, wherein the second magnetic field generator is capable of generating the second magnetic field such that the second magnetic field strength at the carrier surface that is greater than the first magnetic field strength at the carrier surface when the release surface is located a distance of 2 centimeters or less from the carrier surface.

5. A system according to claim 1, wherein the first magnetic field generator comprises magnetic material that generates a static magnetic field.

6. A system according to claim 1, wherein the first magnetic field generator comprises an electromagnet.

7. A system according to claim 1, wherein the second magnetic field generator comprises magnetic material that generates a static magnetic field.

8. A system according to claim 1, wherein the second magnetic field generator comprises an electromagnet.

9. A system according to claim 1, wherein the first magnetic field generator comprises permanently magnetized material and wherein the second magnetic field generator comprises an electromagnet.

10. A system according to claim 9, wherein the second magnetic field generator comprises a controller, wherein the controller changes the second magnetic field strength.

11. A system according to claim 9, wherein the second magnetic field generator comprises a controller, wherein the controller changes the second magnetic field strength according to a predetermined protocol.

12. A method of delivering a therapeutic agent, the method comprising:
 positioning a carrier surface of a carrier device proximate selected internal tissue, wherein magnetic flux lines of a selected magnetic pole of a first magnetic field extend through the carrier surface;
 magnetically retaining a therapeutic agent to the carrier surface, wherein the therapeutic agent is associated with a plurality of magnetic particles;
 positioning a release device that comprises a release surface proximate the selected internal tissue, wherein the selected internal tissue is located between the release surface and the carrier surface, and wherein the release device comprises a second magnetic field generator generating a second magnetic field that extends through the release surface and towards the carrier surface; and
 delivering at least a portion of the therapeutic substance to the selected internal tissue by magnetically attracting at least a portion of the plurality of magnetic particles towards the release surface;
 wherein, proximate the carrier surface, the second magnetic field has a magnetic field strength greater than a magnetic field strength of the first magnetic field;
 and wherein the second magnetic field extending through the release surface comprises a magnetic pole facing the carrier device that is the same as the selected magnetic pole of the carrier device.

13. A method according to claim 12, wherein the method further comprises changing the second magnetic field strength after positioning the carrier surface proximate selected internal tissue.

14. A method according to claim 12, wherein the method further comprises reversing the magnetic pole of the second magnetic field after positioning the carrier surface proximate selected internal tissue.

15. A method according to claim 12, wherein the method further comprises reversing the magnetic pole of the second magnetic field three or more times while the selected tissue is located between the carrier surface and release surface.

16. A method according to claim 12, wherein the first magnetic field strength is substantially constant at the carrier surface.

17. A method according to claim 12, wherein the method further comprises reducing the magnetic field strength of the first magnetic field extending through the carrier surface after positioning the carrier surface proximate the selected internal tissue.

18. A method according to claim 12, wherein the method further comprises terminating the first magnetic field after positioning the carrier surface proximate selected internal tissue.

19. A method according to claim 12, wherein the first magnetic field is generated by magnetic material that generates a static magnetic field.

20. A method according to claim 12, wherein the second magnetic field is generated by magnetic material that generates a static magnetic field.

* * * * *